United States Patent [19]

Smith et al.

[11] Patent Number: 4,471,058

[45] Date of Patent: Sep. 11, 1984

[54] METHOD FOR THE DETECTION AND/OR DETERMINATION OF A POLYVALENT ANTIGEN USING AT LEAST TWO DIFFERENT MONOCLONAL ANTIBODIES

[75] Inventors: William L. Smith, Okemos; David L. DeWitt, East Lansing, both of Mich.

[73] Assignee: Board of Trustees operating Michigan State University, East Lansing, Mich.

[21] Appl. No.: 401,642

[22] Filed: Jul. 26, 1982

[51] Int. Cl.$^3$ .................. G01N 33/54; G01N 33/58
[52] U.S. Cl. .................. 436/518; 436/519; 436/529; 436/548; 436/808; 436/809; 435/240; 435/172.2; 435/68; 435/4; 435/7; 935/110
[58] Field of Search .................. 436/548, 518–523, 436/, 528–534, 547, 548, 804, 808, 815, 823, 828; 422/61; 424/DIG. 1.1; 435/4, 7, 68, 70, 172.2, 240, 241, 170, 810, 948; 935/89, 95, 103, 104, 106, 110

[56] References Cited

U.S. PATENT DOCUMENTS

| | | | |
|---|---|---|---|
| 4,048,298 | 9/1977 | Niswender | 424/1.5 |
| 4,098,876 | 7/1978 | Piasio et al. | 424/1 |
| 4,192,799 | 3/1980 | Fitzpatrick | 260/121 |
| 4,230,685 | 10/1980 | Senyer et al. | 424/12 |
| 4,232,001 | 11/1980 | Jensen et al. | 424/1 |
| 4,244,940 | 1/1981 | Jeong et al. | 424/1 |
| 4,248,965 | 2/1981 | Mochida et al. | 435/7 |
| 4,376,110 | 3/1983 | David et al. | 436/513 |

FOREIGN PATENT DOCUMENTS 44219 1/1982 European Pat. Off. .

OTHER PUBLICATIONS

Smith, W. L. et al., Prog. Lipid Res., vol. 20, pp. 103–110 (1981).
DeWitt, D. L. et al., Methods in Enzymology, vol. 86, pp. 229–240 (1982).
Steensgaard, J. et al., Molecular Immunology, vol. 17, pp. 1315–1318 (1980).
Hurrell, J. C. R. et al., Journal of Immunological Methods, vol. 45, pp. 249–254 (1981).
Nast, Y. et al., Journal of Immunological Methods, vol. 43, pp. 333–341 (1981).
Davies, S. N. et al., Clinical Chemistry, vol. 28 (7), p. 1605, Abstract 281 (1982).
Nomura, M. et al., Molecular Immunology, vol. 19 (12), pp. 1691–1697 (1982).
Moyle, W. R. et al., Proc. National Academy of Sciences, U.S.A., vol. 79, pp. 2245–2249 (4–1982).
Wada, H. G. et al., Clinical Chemistry, vol. 28 (9), pp. 1862–1866 (1982).
Tosi, R. et al., European Journal of Immunology, vol. 11, pp. 721–726 (9–1981) (See Sections 2.5.).
Uotila, M. et al., J. Immunological Methods, vol. 42, pp. 11–15 (4–1981).
Katus, H. A. et al., Molecular Immunology, vol. 19 (3), pp. 451–455 (3–1982).
Ehrlich, P. H. et al., J. Immunology, vol. 28 (6), pp. 2709–2713 (6–1982).

Primary Examiner—Benjamin R. Padgett
Assistant Examiner—M. Moskowitz
Attorney, Agent, or Firm—Ian C. McLeod

[57] ABSTRACT

A method for the detection and/or determination of an antigen having at least two separate antibody combining sites or antigenic determinants (i.e. a polyvalent antigen) using at least two different monoclonal antibodies which bind to the separate sites is described. In particular the method utilizes Protein A with a carrier to immobilize a first monoclonal antibody which in turn, can bind to one antigenic determinant on the antigen. The second antibody with a label is provided in a solution and binds to the second antigenic determinant on the antigen. A test kit is described for practicing the method. Novel anti-PGH synthase and anti-PGI$_2$ synthase antibodies and hybridoma cells producing such antibodies are described.

18 Claims, 4 Drawing Figures

METHOD FOR THE DETECTION AND/OR DETERMINATION OF A POLYVALENT ANTIGEN USING AT LEAST TWO DIFFERENT MONOCLONAL ANTIBODIES

The Government has rights in this invention pursuant to NIH Grants Nos. HD10013 and AM22042 awarded by the Department of Health and Human Services.

BACKGROUND OF THE INVENTION

1. Field of the Invention

A method and test kit for the detection of polyvalent antigens which uses at least two different combining sites on the antigen is described. In particular, novel anti-PGH synthase and anti-PGI$_2$ synthase monoclonal antibodies and hybridoma cells for producing the antibodies are described for use in the method and test kit.

2. Prior Art

Numerous prior art methods are known for using antibodies to detect the presence of a specific antigen. In general, the antigen complexes with the antibody and the complex is separated as a precipitate from non-specified antigenic material. Either the antigen or the antibody is labeled. The presence and/or amount of the label in the precipitated antigen-antibody complex is determined. U.S. Pat. Nos. 4,292,403 and 4,307,071 describe such methods.

The problem with the prior art methods is that the antibodies are usually relatively impure and produce false positive reactions. Also, a single antibody is used for binding the antigen for the detection or determination which allows for error because of the problems with impure or non-specific antibody.

OBJECTS

It is therefore an object of the present invention to provide a novel method and test kit utilizing multiple monoclonal antibodies which provides reliable detection and quantitative determination of polyvalent antigens. Further, it is an object of the present invention to provide novel anti-PGH synthase and anti-PGI$_2$ synthase monoclonal antibodies, which are useful in the method and test kit. It is another object of the present invention to provide novel hybridoma cells which produce the monoclonal antibodies. Finally, it is an object of the present invention to provide hybridoma cells which produce the monoclonal anti-PGH synthase and anti-PGI$_2$ synthase monoclonal antibodies. These and other objects of the present invention will become increasingly apparent from the following description and the drawings.

IN THE DRAWINGS

SUMMARY OF THE INVENTION

Figure 1:
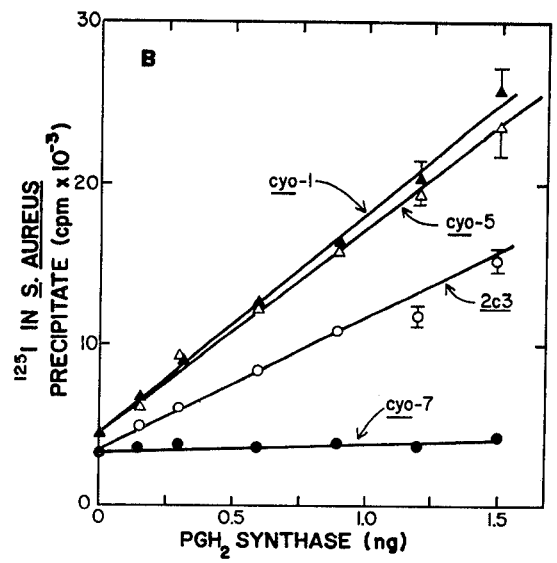
FIG. 1 is a graph showing PGH synthase concentration as a function of first antibody-second antibody complex precipitate.

The present invention relates to an improved method for determination of polyvalent antigens by reaction with monoclonal antibodies specific for the antigen, wherein the antigen has at least two separate different binding sites for the antibodies (which makes it polyvalent) which comprises:

providing a first antibody which combines with a first polyvalent antigen site and which is bound to an immobilizing carrier and a second antibody in solution which combines with a second combining site on the antigen and not to the carrier and which is labeled so as to be detectable, wherein the antibodies are produced by different hybridoma cells and are specific for the same antigen but having different combining sites on the antigen;

reacting the antigen in a solution with the first antibody bound to the carrier to provide a first antibody-antigen complex with the carrier;

reacting the first complex with the second antibody in a solution to provide a first and second antibody-antigen complex with the carrier which is separable from the solution;

separating the first antibody-second antibody-antigen complex from unbound second antibody in solution; and determining the presence of label in the first antibody-second antibody-antigen complex.

Further the present invention relates to a test kit for a polyvalent antigen which comprises:

a first monoclonal antibody bound to protein A immobilized on a carrier; and a labeled second monoclonal antibody in a solution, wherein in use the amount of the second antibody which combines with the antigen is determined by the label in direct correlation with the amount of antigen and wherein the first and second antibodies are produced by different hybridoma cells and are both specific for the same antigen but bind different antigenic determinants on the antigen.

The present invention also relates specifically to anti-PGH synthase antibody producing hybridoma cells cyo 1, 3, 5 and 7 deposited as ATCC HB 8124, HB 8125, HB 8126 and HB 8127, respectively. The American Type Culture Collection (ATCC) is located in Rockville, Md. The present invention further relates to anti-PGI2 synthase antibody producing hybridoma cells isn-1 and isn-3 deposited as ATCC HB 8123 and HB 8122, respectively.

Finally, the present invention provides the anti-PGX synthase monoclonal antibody producing hybridoma cells of fused myeloma and spleen cells producing anti-PGX synthase antibody, wherein the spleen cells are derived from mice which have been injected with PGX synthase and wherein X is H or I$_2$.

In the method of the present invention the immobilizing carrier is preferably a protein A containing composition. The carrier can be cells of *Staphylococcus aureus* containing protein A, which have been killed and fixed in a manner to retain their structural integrity and which bind directly to the first antibody without interfering with its antigenic binding capability. *Staphylococcus aureus* ATCC 12598 is preferred. In general the cells are attenuated (live or killed cell) in some manner. Another example of a carrier is Sepharose CL-4B or any other inert matrix or bead to which protein A can be covalently bound so as to function in the same manner as the *Staphylococcus aureus*. Generally there are fewer protein A binding sites.

The first antibody is reacted with the carrier protein A in a molar excess over what is necessary to bind all of the available sites and then the excess unreacted antibody is removed by washing the carrier (cells) in preparation for use in the test kit. The use of protein A for binding antibodies is described by Kessler, S. W. *J. Immunol.* 115, 1617 (1975).

As described more fully hereinafter in the Examples, the monoclonal antibody is preferably produced by hybridoma cells cyo 1, 5 or 7 or isn-1. These hybridoma cells are produced by the fusion of myeloma cells with spleen cells from an animal which have been injected with the specific antigen in order to induce the antibody reaction in the spleen cells. The antigen is preferably purified PGH synthase or PGI$_2$ synthase. The myeloma and spleen cells are preferably from mice; however, as will be appreciated by those skilled in the art other cell sources and antigens can be used in the method of the present invention.

The hybridoma cells are usually isolated from multiple animals of the same species by injecting the antigen in order to obtain antibodies which differ as to the binding site on the same antigen. Most enzyme antigens are polyvalent (i.e. have multiple binding sites for antibodies) and the present method and test kit relies upon the recognition of the availability of these combining sites.

In some instances the monoclonal antibody will not bind directly with protein A. In this event, a linking or conjugal antibody is used to bind the first monoconal antibody to the carrier. Thus, the first antibody must bind the conjugal antibody which in turn binds the protein A of the carrier. This step is used with the PGI$_2$ synthase test kit. Preferably the conjugal antibody is conjugal anti-mouse antibody when the first antibody is derived from mouse spleen cells and can be obtained from rabbits or other animal antibody sources as is known to those skilled in the art.

The carrier can be provided as an aqueous suspension or it can be fixed as a coating on a surface such as a well in a test kit. The coating provides a site for the easy application of a solution of a first monoclonal antibody in determining the presence of the antigen of interest. All of this is well known to those skilled in the art.

The second monclonal antibody is also specific for the same polyvalent antigen as the first antibody but binds a different antigenic site. A label, such as $I^{125}$ is provided as a means for detecting the presence and amount of the second antibody which binds to the antigen first antibody-carrier complex. The use of labels such as enzymes such as $\beta$-galactosidase or radioisotopes (e.g. $^{125}I$), is well known to those skilled in the art. The amount of label in the second antibody-antigen-first antibody-carrier complex can be quantitated after a specific uniform reaction incubation time between the labeled second antibody and the immobilized antigen which is usually between about 5 and 180 minutes. Excess unbound labeled second antibody is removed from the second complex before the determination. Preferably the protein A of the carrier or the conjugal antibody does not bind with the second antibody, although it is possible to conduct the second antibody reaction rapidly enough to prevent substantial reaction of the second antibody with the protein A or the conjugal antibody.

DESCRIPTION OF PREFERRED EMBODIMENTS

EXAMPLE 1

Anti-PGH synthase monoclonal antibodies

Experimental Procedures

Materials. Trypticase ® soy broth soybean-casein digest media was from BBL Microbiology Systems, Cockeyville, Md. The following reagents were obtained from Sigma Chemical Company of St. Louis, Mo.: hypoxanthine, penicillin, streptomycin sulfate, aminopterin, thymidine and 6-thioguanine. Fetal calf serum was from KC Biologicals, Inc. of Lenexa, Kans. Seaplaque agarose was from Marine Colloid Inc., Rockland, Me. Freund's adjuvants, Hank's balanced salt solution and Dulbecco's modified Eagle medium (DMEM) containing D-glucose (4.5 g/l) and L-glutamine (2 mM) were purchased from Grand Island Biological Co. of Grand Island, N.Y. NCTC 109 medium was from Microbiological Associates, Bethesda, Md. Normal horse serum was from Flow Laboratories of Dublin, Va. Fluorescein isothiocyanate (FITC)-labeled rabbit anti-mouse IgG, rabbit anti-mouse IgG, IgG$_1$, IgG$_{2a}$ and IgG$_{2b}$ were obtained from Miles Laboratories of Elkhart, Ind. Protein A-Sepharose was purchased from Pharmacia Fine Chemicals of Uppsala, Sweden. Bolton and Hunter's reagent (1400 Ci/mmole) was from Amersham of Arlington Heights, Ill.

Cell lines, animals, tissues. Female C57BL mice (4–6 weeks old) were from Jackson Laboratories of Bar Harbor, Me. and female albino Swiss mice (4–6 weeks old) were from Spartan Animal Services, Michigan State University. Sheep vesicular glands and bovine seminal vesicles were obtained from a local abattoir and stored at $-80°$. Outdated human platelet concentrates donated by the Lansing, Michigan Regional Red Cross Blood Distribution Center, were washed with Hank's balanced salt solution containing 1% EDTA, pH 7.4 prior to preparation of microsomes. Female sprague-Dawley rats (150–200 g), female New Zealand white rabbits (2 kg) and virgin female guinea pigs (600–800 g) were obtained from local animal suppliers, SP2/O-Ag14 deposited as ATCC CRL-1581, an 8-azaguanine-resistant myeloma strain was obtained from the Cell Distribution Center of the Salk Institute, LaJolla, Calif. Swiss mouse 3T3 fibroblasts (ATCC CCL 92) were from the ATCC. Rats and guinea pigs were killed by decapitation, mice by cervical dislocation and rabbits by intravenous injection of 5% phenobarbitol.

Preparation of microsomes. All steps were performed at 4°. Rabbit or guinea pig kidney, rat small intestine, bovine seminal vesicles, sheep vesicular glands or human platelets were homogenized in 5–10 volumes of 0.1 M Tris-chloride, pH 8.0, containing 20 mM diethyldithiocarbamate and 1 mM phenol. Platelets were homogenized in a glass homogenizer with sonication in a Cole-Parmer ™ ultrasonic cleaner. Other tissues were homogenized using a Polytron ™ homogenizer. The homogenates were centrifuged at $10,000 \times g$ for 10 minutes and the resulting supernatants centrifuged at $200,000 \times g$ for 35 minutes. The resulting microsomal pellets were resuspended by homogenization in starting buffer to a protein concentration of 1–10 mg/ml as determined by the Coomassie Blue protein assay procedure. If cyclooxygenase activity was to be solubilized, Tween ™ 20 was added to the resuspended microsomes to give a final concentration of 1.0% (w/v) detergent.

Myeloma-spleen cell fusions. Fusions were performed by modification of a method of Galfre et al., Nature, 266, 550 (1977). Four to six week old female C57/BL mice or Swiss albino mice were immunized (i.p.) at two week intervals with 20 micrograms of PGH synthase purified from sheep vesicular gland and suspended in complete Freund's adjuvant. Three days after the third innoculation the mice were killed by cervical dislocation and their spleens removed under sterile conditions. The spleens were placed in 5 ml of Dulbecco's modified Eagle essential minimal media (DMEM) containing 20 mM HEPES (4-(2-hydroxyethy)-1-piperazine ethane sulfonic acid), pH 7.6, cut into pieces (1 cm$^3$) and then teased apart with twissors to release the lymphocytes. After vortexing the mixture, the large tissue fragments were allowed to settle briefly. The supernatant containing the lymphocytes was then centrifuged at $1000 \times g$ for 5 minutes. Red blood cells in the pellet were removed by hypotonic lysis with 5.0 ml of 0.2% saline for 30 seconds followed by 5.0 ml of 1.6% saline for 30 seconds. Finally, 10 ml of DMEM containing 20 mM HEPES, pH 7.6 was added and the remaining spleen cells were then collected by centrifugation and resuspended in DMEM containing 20 mM HEPES, pH 7.6.

The mouse myeloma strain SP2/O-Ag14 was grown in DMEM containing 10% fetal bovine serum and 100 milligrams per liter each of penicillin and streptomycin at 37° under a water-saturated 5% $CO_2$ atmosphere. SP2 myeloma cells ($1-5 \times 10^6$), which had been washed and resuspended in DMEM plus 20 mM HEPES pH 7.6, were mixed with $1-5 \times 10^7$ of the isolated splenic lymphocytes. The cell mixture was collected by centrifugation at $1000 \times g$ for 5 minutes in a sterile glass centrifuge tube. After removing the supernatant, the fusion was begun by gently shaking the cell pellet, largely intact, with a solution containing 35% polyethylene glycol 1000 (Baker) and 5% dimethylsulfoxide in DMEM for 1 minute. During the ensuing 3 minutes the fusion solution was diluted with 3 ml of serum-free DMEM; then, over a period of 6 minutes, the fusion mixture was diluted further with 12 ml of DMEM containing 20% fetal bovine serum. Finally, the cells were collected by centrifugation, resuspended in 48 ml of HT media (DMEM) containing 10% (v/v) fetal bovine serum, 10% (v/v) horse serum, and 10% (v/v) NCTC 109 media, 2 mM glutamine, 100 microM hypoxanthine, 16 microM thymidine, 3 microM glycine, 100 mg/l penicillin and 100 mg/l streptomycin) and dispensed into 2-24 well Costar 3524 cluster tissue-culture plates. After 24 hours, an additional 1 ml of HAT Media (HT media plus 1 microM aminopterin) was added to each well. Half of the media was replaced with fresh HAT media 2 and 4 days thereafter; 14-21 days after the cell fusion, when the media from those wells with growing hybridomas began to acidify (turn yellow), aliquots of media were removed to test for the presence of anti-PGH synthase antibody.

Selection of hybridomas producing antibody to PGH synthase. The Protein-A bearing Cowen I strain of Staphylococcus aureus ATCC 12598 were grown in Trypticase TM soy broth soybean-casein digest media and attenuated as described by Kessler, J. Immunol. 117, 1482 (1976). Formaldehyde-fixed, heat-killed Staphylococcus aureus cells were stored at −80° as a 10% cell suspension in 10 mM HEPES, pH 7.5 containing 150 mM NaCl. Prior to the immunoprecipitation assays, 1.0 ml aliquots of the cell suspensions were defrosted and washed by sequential centrifugation and resuspension as follows: (a) twice with 1 ml of 0.1 M Tris-chloride, pH 8.0 containing 5% bovine serum, (b) twice with 1 ml of 0.1 M Tris-chloride, pH 8.0 containing 1% Tween 20 (w/v); (c) once with 1 ml of 0.1 M Tris-chloride, pH 8.0 containing 1% Tween 20 TM (w/v) and 80 micrograms of rabbit anti-mouse IgG and (d) twice with 1 ml of 0.1 M Tris-chloride, pH 8.0 containing 1% Tween 20 TM (w/v). Finally the cells were resuspended in 1 ml of 0.1 M Tris-chloride, pH 8.0 containing 1% Tween 20 TM (w/v).

For assay, 0.1 ml of the rabbit anti-mouse IgG-Staphylococcus aureus suspension was mixed with 0.1 ml of the media removed from each well with growing hybridomas. The sample was vortexed and then centrifuged for 2 minutes at $500 \times g$ on a desk-top centrifuge. A volume of solubilized sheep vesicular gland microsomes (ca. 0.005 ml) containing 25 units of cyclooxygenase activity was added to the Staphylococcus aureus pellet along with 0.1 M Tris-chloride, pH 8.0 containing 20 mM diethyldithiocarbamate and 1 mM phenol to give a final volume of 0.1 ml. The mixture was vortexed and then centrifuged to pellet the cells. The supernatant was removed and the resulting pellet was resuspended in 0.1 ml of starting buffer. Both the supernatant and pellet were assayed for cyclooxygenase activity. Precipitation of cyclooxygenase activity was taken as evidence that at least some of the hybridoma cells present in the test well were producing anti-PGH synthase antibodies.

Cells from wells yielding positive responses in the immunoprecipitation test were cloned in soft agar using Swiss mouse 3T3 cells as a feeder layer. Cells from individual clones were cultured and the media retested for anti-PGH synthase activity as described above. A few positive clones from each positive well were cultured, frozen and stored in liquid $N_2$.

Immunofluorescence staining for PGH synthase. Media from hybridoma clones secreting anti-PGH synthase antibodies were used in an indirect immunofluorescence procedure to detect the PGH synthase antigen in kidney sections. Sections (10 $\mu$m) from rabbit, rat, mouse and guinea pig kidney were cut on a Tissue-Tek TM cryotome and stained for cyclooxygenase (PGH synthase) antigenicity using sequential incubations with media from hybridoma cells (1:5 dilutions in 0.1 M sodium phosphate, pH 7.0) and then fluorescein-isothiocyanate (FITC)-labeled rabbit anti-mouse IgG (1:20 dilution in 0.1 M sodium phosphate, pH 7.0) essentially as described previously for rabbit anti-cyclooxygenase serum (Smith and Bell, Am. J. Physiol. 235, F451 (1978)). Interaction of antibody with the PGH synthase was indicated by the appearance of fluorescence in renal medullary collecting tubules and interstitial cells in experimental but not control samples. Media from hybridoma-containing cultures which failed to cause immunoprecipitation of sheep vesicular gland PGH synthase were used as control media. A Leitz TM Orthoplan microscope was used to visualize fluorescent staining.

Preparation of IgG-free fetal calf serum and cell culture media. Fetal calf serum (100 ml) was adjusted to pH 8.2 and applied to a Protein A-Sepharose CL-48 column ($1 \times 5$ cm) equilibrated with 0.1 M sodium phosphate, pH 8.0. The eluant was collected and bovine IgG absorbed to the column was then removed by washing with 2-3 column volumes of 0.1 M sodium citrate, pH 3.5. The column was reequilibrated with 0.1 M sodium phosphate, pH 8.0, and the entire procedure repeated. After three passages of fetal calf serum through the column, no IgG detectable by Ouchterlony double-diffusion analysis with rabbit anti-bovine IgG was found to elute with 0.1 M sodium citrate, pH 3.5. Media used for isolation of mouse IgG was standard HT media containing 20% IgG-free fetal calf serum and no horse serum.

Purification of mouse IgG from hybridoma culture media. Media from cyo-3 hybridoma cell cultures (free of bovine IgG) was adjusted to pH 8.2 and applied to a Protein A-Sepharose CL-4B column ($1 \times 5$ cm). Absorbed material was eluted stepwise using 0.1 M buffers of pH 8.0 (sodium phosphate) pH 6.0, pH 4.5, and pH 3.5 (sodium citrate). Anti-PGH synthase activity in each fraction was monitored by measuring the ability of aliquots of the fraction when mixed with rabbit anti-mouse IgG-*Staphylococcus aureus* complexes to precipitate cyclooxygenase activity. $IgG_1$ secreted by hydridoma line cyo-3 was eluted at pH 6.0. Fractions containing $IgG_1$ were pooled, dialyzed overnight against 0.125 M sodium borate, pH 8.4, and stored at $-80°$. In one experiment in which cyo-3 were grown to confluency, 9 mg of $IgG_1$ (as determined by the absorbance at 280 nm ($\epsilon = 1.4$ (mg/ml)$^{-1}$) was isolated from 120 ml of media; 1 µg of isolated $IgG_1$ when bound to 0.1 ml of the rabbit anti-mouse igG-*Staphylococcus aureus* cell sespension was able to bind 18 units (ca. 0.6 µg) of cyclooxygenase activity.

Radioiodination of $IgG_1$ (cyo-3) and sheep vesicular gland microsomes. Both $IgG_1$ and sheep vesicular gland microsomes were radioiodinated essentially as described by Bolton and Hunter. For routine iodinations, an aliquot containing 0.4 mCi of Bolton and Hunter's reagent was evaporated under a gentle stream of dry $N_2$ in a $6 \times 50$ mm test tube. $IgG_1$ (40 µg, cyo-3) or solubilized sheep vesicular gland microsomes (400 g of protein) in 0.01–0.05 ml of 0.125 M sodium borate, pH 8.4 was added and the sample incubated at 4° for 15 min with frequent agitation. Unreacted iodinating reagent was destroyed by the addition of 0.5 ml of 0.2 M glycine to the reaction buffer followed by a 10 minute incubation at 4°. Products were separated by chromatography on a column of Biogel P-30 ($0.5 \times 7$ cm) eluting with 0.05 M sodium phosphate, pH 7.4 containing 2.5 mg/ml gelatin and 0.02% $NaN_3$. Fractions eluting at the void volume were pooled and stored at $-80°$ in small aliquots (0.2 ml) containing 12-20 microCi. The percentage of radiolabel incorporated into $IgG_1$ or microsomal protein using this procedure ranged from 60–80%; most (ca. 80%) of the $^{125}I$ present in $IgG_1$ coelectrophoresed with the heavy chain on SDS-gel electrophoresis. Prior to use of $^{125}I$-$IgG_1$ for immunoradiometric assays, samples were thawed and diluted in 0.05 M sodium phosphate, pH 7.4 containing 2.5 mg/ml gelatin.

Immunoradiometric assay of PGH synthase. A 10% (w/v) suspension of attenuated *Staphylococcus aureus* cells was washed by centrifugation once in 0.1 M Tris-chloride, pH 7.4 containing 5% (w/v) BSA and 1% Tween-20 TM, and then twice in 0.1 M Tris-chloride, pH 7.4 with 1% Tween-20 TM (the assay buffer) followed by resuspension to 10% (w/v) *Staphylcoccus aureus* in the assay buffer. Equal volumes of washed *Staphyloccus aureus* suspensions and media from various $IgG_2$-producing hybridoma clones (cyo-1,5,7 or 2c3) were mixed, allowed to stand 15 min at 24° and then centrifuged. Pellets were resuspended and washed twice in the assay buffer and finally resuspended to 10% (w/v) *Staphylococcus aureus* concentration.

Solubilized microsomes were diluted into 0.1 ml of assay buffer to contain the equivalent of 0.005-0.05 units of cyclooxygenase activity: 0.1 ml of *Staphylococcus aureus* -$IgG_2$ complex preparation (sufficient to bind 3 units of cyclooxygenase activity) was then added. Finally, 0.01 ml of $^{125}I$-$IgG_1$ (cyo-3), containing 50,000 $^{125}I$ cpm originally (this amount was not altered to compensate for decay of the $^{125}I$) was added. Assay mixtures were incubated at 4° overnight. Pellets were collected by centrifugation, washed once in 0.2 ml of assay buffer and recentrifuged. The supernatants were removed by aspiration, and the tubes containing the pellets were inserted into vials and counted using a Beckman Biogamma TM Y-counter.

SDS Polyacrylamide Gel Electrophoresis. Samples were resolved in 7.5% polyacrylamide gels in the presence of 0.1% SDS by a modification of the method of Laemmli (*Nature*, 227, 680 (1971). Washed immunoprecipitates obtained after incubating rabbit anti-mouse IgG, mouse monoclonal $IgG_2$ and $^{125}I$-labeled microsomes were suspended in 0.025 ml of 10% SDS; 0.002 ml of 2-mercaptoethanol, 0.003 ml of 0.2% bromphenol blue, 0.010 ml of glycerol and 0.010 ml of 1.5 M Tris-chloride, pH 8.0, containing 10–20 micro g of protein standards were added prior to heating at 100° for 2 min. Electrophoresis was performed in 0.5 mm (i.d.) tubes at 1.5 mA per gel. Protein standards (e.g. PGH synthase) were detected by staining with Coomassie blue. Following destaining to visualize standards, gels were cut in 2 mm sections and counted on a Beckman Biogamma TM Y-counter.

Ouchterlony double-diffusion and immunoprecipitation analyses. Double diffusion analyses were performed in 1.5% Bacto-agar containing 0.02% $NaN_3$. Media (0.04 ml) from hybridoma cultures and rabbit anti-mouse $IgG_{2a}$, $IgG_{2b}$ b or $IgG_1$ serum (0.04 ml) were placed in adjacent wells and allowed to diffuse at 24° for 16-24 hours prior to analysis. Immunoprecipitation of IgG produced by mouse hybridomas was performed by incubating 0.005 ml rabbit anti-mouse IgG and various amounts (0.01-0.1 ml) of culture media with enough 0.1 M Tris-chloride, pH 7.4, containing 0.1% Tween 20 TM to make a final volume of 0.5 ml. The samples were incubated overnight at 4°, collected by centrifugation at $2000 \times g$ for 15 minutes and washed once with starting buffer.

RESULTS AND DISCUSSION

Isolation of hybridoma cell lines secreting anti-PGH synthase IgG. Two separate fusions of SP2/O-Ag14 plasmacytomas with splenic lymphocytes from mice immunized with purified PGH synthase were performed. In the first fusion, lymphocytes were obtained from a C57BL mouse; in the second, lymphocytes were obtained from an outbred strain of Swiss white mice. Media from 48 different hybridomas obtained in the first fusion were tested for anti-PGH synthase activity by mixing the media with rabbit anti-mouse IgG-*Staphylococcus aureus* complexes, and then testing the resulting complexes for their abilities to precipitate solubilized cyclooxygenase activity; one hybridoma (cyo-1) was ultimately cloned from the first fusion. Three additional clones (cyo-3, cyo-5 and cyo-7) secreting anti-PGH synthase antibody were prepared from hybridomas obtained in the second fusion after screening media from 24 different hybridoma-containing wells.

An additional hybridoma (2c3) was obtained from the first fusion. IgG secreted by 2c3 does not interact with the PGH synthase, and thus, 2c3 was used as a negative control in subsequent immunochemical tests.

The cells are deposited with the ATCC, Rockville, Md. as follows:

| | |
|---|---|
| cyo-1 | HB-8124 |
| cyo-3 | HB-8125 |
| cyo-5 | HB-8126 |
| cyo-7 | HB-8127 |

In our initial screen for hybridomas secreting anti-PGH synthase activity, we used a *Staphylococcus aureus*-rabbit anti-mouse IgG complex to precipitate mouse IgG from the culture media. Thus, it was unclear what subclass of mouse antibody was secreted by the different lines. Single lines of immunoprecipitation were obtained when media from cyo-1, cyo-5 or cyo-7 were tested by Ouchterlony double-diffusion analysis against both rabbit anti-mouse $IgG_{2b}$ sera; however, media from these latter clones failed to react with rabbit anti-mouse $IgG_1$ serum. In contrast, media from cyo-3 gave a single line of precipitation with rabbit anti-mouse $IgG_1$ serum but was unreactive with either anti-$IgG_{2a}$ or anti-$IgG_{2b}$ sera. These results suggested that cyo-1,5 and 7 produce $IgG_2$ molecules and that cyo-3 produces an $IgG_1$. Media from cyo-1, cyo-3 and cyo-5 were examined further by observing the behavior of these different anti-PGH synthase monoclonal antibodies upon column chromatography on Protein A-Sepharose. As expected, $IgG_{2b}$ secreted by cyo-1 and cyo-5 culture media were eluted between pH 3.0 and 3.5 and not between pH 4.0 and 4.5. Thus, the IgG molecules produced by cyo-1 and cyo-5 are of the $IgG_{2b}$ subclass. The results of the subclass analyses of different hybridoma lines are summarized in Table I.

TABLE I

| Analysis of Monoclonal Antibodies Against PGH Synthase. | | |
|---|---|---|
| Antibodies produced by hybridoma line: | aSubclass | bReactivity with PGH synthase from |
| cyo-1 | $IgG_{2b}$ | Positive: sheep, bovine, human, rat Negative: guinea pig, rabbit, mouse, dog |
| cyo-3 | $IgG_1$ | Positive: sheep, bovine, human, guinea pig, rabbit Negative: rat, mouse, dog |
| cyo-5 | $IgG_{2b}$ | Positive: sheep, bovine, human, guinea pig, rabbit Negative: rat, mouse, dog |
| cyo-7 | $IgG_2$ | Positive: sheep, bovine, human, guinea pig, rabbit Negative: rat, mouse, dog |
| 2c3 | $IgG_2$ | negative with all species | adetermined on the basis of Ouchterlony double-diffusion analyses with rabbit anti-mouse $IgG_1$, $IgG_{2a}$ and $IgG_{2b}$ antisera and elution profiles from Protein-A Sepharose.
bdetermined by immunoprecipitation of solubilized cyclooxygenase activity from sheep vesicular gland, rat small intestine, rabbit renal medulla, guinea pig renal medulla, bovine seminal vesical and human platelet microsomes and/or by immunofluorescent staining using rat, dog, mouse, guinea pig and rabbit kidneys.

(a) determined on the basis of Ouchterlony double-diffusion analyses with rabbit anti-mouse $IgG_1$, $IgG_{2a}$ and $IgG_{2b}$ antisera and elution profiles from Protein-A Sepharose.

(b) determined by immunoprecipitation of solubilized cyclooxygenase activity from sheep vesicular gland, rat small intestine, rabbit renal medulla, guinea pig renal medulla, bovine seminal vesicle and human platelet microsomes and/or by immunofluorescent staining using rat, dog, mouse, guinea pig and rabbit kidneys.

Also summarized in Table I are data indicating the reactivities of different anti-PGH synthase immunoglobulins with PGH synthases (cyclooxygenases) from different animals. The pattern of species cross-reactivities was the same for IgGs secreted by cyo-3, cyo-5 and cyo-7 which was, in turn, different from that of IgG produced by cyo-1. Thus, $IgG_{2b}$ secreted by cyo-1 reacts with a determinant different from the determinant(s) which interact with IgGs produced by other hybridoma lines.

Figure 3:
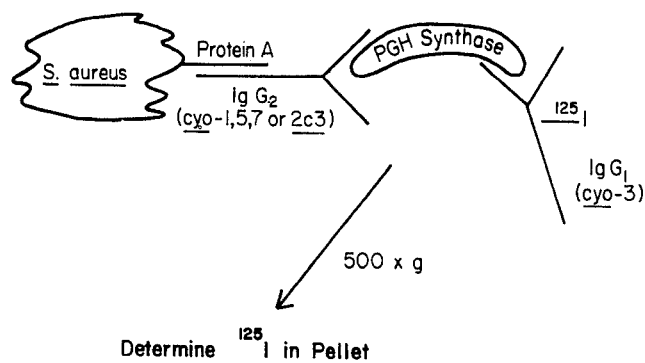
FIG. 3 is an illustration showing the complexes of FIG. 1.

We developed an immunoradiometric assay for quantitating PGH synthase. The results of this assay indicate that IgGs secreted by cyo-3 and cyo-7 interact with an overlapping determinant but that cyo-5 produces an antibody which reacts with yet another antigenic site; thus, different hybridoma strains produce antibodies against three distinct antigenic sites on the PGH synthase. The immunoradiometric assay is pictured schematically in FIG. 3. $IgG_1$ secreted by cyo-3 was isolated from culture media and then labeled with $^{125}I$-Bolton-Hunter reagent. Fixed amounts of $^{125}I$-$IgG_1$ (cyo-3) were incubated with (a) fixed amounts of a precipitating complex prepared by affixing $IgG_2$ from cyo-1, cyo-5, cyo-7 or 2c3 to attenuated *Staphylococcus aureus* cells and (b) varying levels of PGH synthase. The amount of cell-bound (precipitated) $^{125}I$ was then determined (FIG. 1). The samples were incubated at 4° overnight, the cell pellets collected and washed and cell-bound radioactivity quantitated. Precipitating complexes were with $IgG_2$ secreted by: 4—4, cyo-1; 4—4, cyo-5; 0—0, 2c3 and 5—5, cyo-7.

Substantial precipitation of $^{125}I$-$IgG_1$ occurs with the $IgG_2$ (2c3)-*Staphylococcus aureus* complex. This latter result also occurred when *Staphylococcus aureus* cells alone were substituted for the $IgG_2$ (2c3)-*Staphylococcus aureus* cells complex indicating that small amounts of the PGH synthase are bound to *Staphylococcus aureus* cells in the absence of an intervening antibody. However, the fact that no binding of $^{125}I$-$IgG_1$ occurs with enzyme bound to the $IgG_2$ (cyo-7)-*Staphylcoccus aureus* complex suggests that the enzyme preferentially binds via antibody directed against it when such an antibody is present on the *Staphylcoccus aureus* cells.

A positive, linear relationship between precipiated $^{125}I$ and purified PGH synthase existed over the range of 0.0045–0.045 cyclooxygenase units (0.15–1.5 ng; slope=765,000 cpm/unit) when using either the $IgG_{2b}$-(cyo-1- or cyo-5)-*Staphylococcus aureus* cells as precipitating complexes; however, minimal $^{125}I$ above control levels was bound using the $IgG_2$ (cyo-7)-*Staphylococcus aureus* complex. Virtually identical slopes (i.e. cpm/unit) were obtained using both the purified enzyme and solubilized sheep vesicular gland microsomes. The observation that binding of $^{125}I$-$IgG_1$ (cyo-3) cannot occur to enzyme that is bound to *Staphylococcus aureus* cells via the $IgG_2$ secreted by cyo-7 suggested that cyo-3 and cyo-7 secrete immunoglobulins directed against the same site. In fact, IgGs produced by cyo-3 and cyo-7 apparently do bind the same or, at least, overlapping sites. Adsorption of intact sheep vesicular gland microsomes with an excess of $IgG_2$ secreted by cyo-7 prevents subsequent binding of $^{125}I$-$IgG_1$ (cyo-3); in contrast, adsorption of microsomes with $IgG_{2b}$ molecules secreted by cyo-1 and cyo-5 did not interfere with $^{125}I$-$IgG_1$ (cyo-3) binding.

EXAMPLE 2

Anti-$PGI_2$ Synthase Monoclonal Antibodies

In this example the preparation of two hybridoma lines producing monoclonal antibodies against two different antigenic sites on the $PGI_2$ synthase enzyme molecule is described. The hybridoma lines were derived from mice immunized with a partially purified preparation of $PGI_2$ synthase from bovine aorta. Using these antibodies we have developed an immunoradiometric assay with which to quantitate $PGI_2$ synthase protein concentrations. This assay is 50-100 times more sensitive than conventional radiochromatographic enzyme activity assays.

$PGI_2$ Synthase Purification

Bovine aorta obtained fresh at slaughter is frozen immediately on dry ice, then stored at −80°. The abdominal region of the aorta beginning 15-20 cm from the heart is easiest to homogenize. Frozen aorta is fractured into small pieces (ca. 2 cm$^3$) with a hammer and homogenized in 2-3 volumes of ice-cold 0.1 M Tris-chloride, pH 8.0 containing $10^{-4}$ M Fluribiprofen (or any other PGH synthase inhibitor at an inhibitory concentration) with a Polytron ™ (Brinkmann) homogenizer. Care should be taken to maintain the buffer temperature below 5° during homogenization. The homogenate is centrifuged at 10,000 g for 10 minutes and the resulting supernatant is centrifuged for 35 minutes at 200,000 g to collect the microsomal pellet. When stored at −80° the pellets retain their $PGI_2$ synthase activity for 2 to 3 months.

Further purification of $PGI_2$ synthase is performed using a modification of the method of Wlodawer and Hammarstrom (FEBS Lett 97,32 (1979)). Microsomal pellets (0.5 g) from 25 to 30 g of tissue are resuspended with a glass homogenizer in 10 ml of 0.1 M Tris-chloride, pH 8.0, containing $10^{-4}$ M Fluribiprofen. This homogenate is centrifuged at 200,000 g for 35 minutes. The washed pellet is resuspended in 10 ml of 10 mM sodium phosphate, pH 7.4, containing 0.5% Triton X-100 ™ (Calbiochem-Behring, LaJolla, Calif.) and again centrifuged at 200,000 g for 35 minutes. The supernatant is removed, and the solubilized $PGI_2$ synthase is applied to a DE-52 cellulose (Whatman Inc., Clifton, N.J.) column (2×8 cm) equilibrated with 10 mM sodium phosphate, pH 7.4, containing 0.1% Triton X-100; the column is then washed with 60 ml of the equilibration buffer. $PGI_2$ synthase is eluted with 0.2 M sodium phosphate, pH 7.4 containing 0.1% Triton X-100 ™. The specific activity of the $PGI_2$ synthase at this step ranges from 100 to 225 with an average of 150 units per milligram of protein per minute. One unit of activity is defined as that amount of enzyme that will catalyze the formation of 1 nmol of $PGI_2$ per minute under standard assay conditions. This represents a purification of approximately 10-fold. A summary of a typical purification is presented in Table II.

TABLE II

| Step | Partial Purification of $PGI_2$ Synthase | | | |
|---|---|---|---|---|
| | Protein concentration (mg/ml) | Specific activity (nmol of 6-keto-$PGF_1$ $min^{-1}$ $mg^{-1}$ protein) | Recovery of activity (%) | Purification (fold) |
| 1. 10,000 g supernatant of homogenized aorta | 4.5 | 12 | 100 | — |
| 2. Microsomal suspension (0.1 M Tris-chloride pH 8.0) | 3.9 | 23 | 45 | 2 |
| 3. 20,000 g supernatant of solubilized microsomes | 1.05 | 94 | 41 | 7.8 |
| 4. Eluant from DE-52 column | 0.73 | 110 | 24 | 9.2 |

Immunization Protocol

Partially purified $PGI_2$ synthase (through DE-52 chromatography) is used for immunization of outbred 4 to 6 week-old female ICR Swiss white mice (Harlan Laboratories). Approximately 250 μg of protein (average specific activity of 150 units per milligram of protein) in 0.2 ml of 0.2 M phosphate, pH 7.4, containing 0.1% Triton X-100 ™ is emulsified by sonication with 200 μl of complete Freund's adjuvant (GIBCO) and injected intraperitoneally. After 2-4 weeks the mice are again inoculated using $PGI_2$ synthase emulsified in incomplete Freund's adjuvant. Three days after the second booster, mice are killed by cervical dislocation. Spleens are removed asceptically, and blood is collected to test for anti-$PGI_2$ synthase activity. Spleen cells from all mice are fused, but only those hybridomas from mice found to have anti-$PGI_2$ synthase activity in their serum are screened for anti-$PGI_2$ synthase activity.

Fusion of Mouse Spleen cells

Spleen cells (1 to 5×10$^7$) from mice inoculated with $PGI_2$ synthase are fused with 1 to 5×10$^6$ HGPRT-negative SP2/O-Ag14 mouse myeloma cells (ATCC CRL 1581) as described above for PGH synthase but with the following modifications. After fusion, cells are suspended in 90 ml of complete HT medium and distributed into six 96-well tissue culture plates (Costar Cambridge Mass.). After 24 hours, 150 microliters (μl) of complete HAT medium (complete HT medium containing 1 microM aminopterin) are added to each well. Two and four days thereafter, 150 μl of medium is removed from each well and replaced with 150 microliters of fresh complete HAT medium. When the medium in a well with growing hybridomas begins to turn yellow (12-15 days after fusion), 200 microliters of the spent medium are removed to test for anti-PGI$_2$ synthase antibody. The medium is replaced with 200 microliters of complete HAT medium.

Assay for Monoclonal Antibodies Against PGI$_2$ Synthase

*Staphylococcus aureus* cells conjugated with rabbit anti-mouse IgG (Miles, Elkhart, Ind.) can bind and precipitate all subclasses of mouse IgGs. When mixed with medium containing mouse anti-PGI$_2$ synthase antibody, the newly formed *Staphylococcus aureus*-rabbit anti-mouse IgG-mouse IgG complex will precipitate solubilized PGI$_2$ synthase. This precipitate can be assayed for PGI$_2$ synthase activity Immunoglobulin classes other than IgG are not detected by this method.

*Staphylococcus aureus* (Cowan strain I) are grown and attenuated by the method of Kessler as described by DeWitt et al (*J. Biol Chem.* 256, 100375 (1981)). The rabbit anti-mouse IgG-*Staphylococcus aureus* complexes are prepared by washing, collecting (by centrifugation), and resuspending 5 ml of a 10% *Staphylococcus aureus* cell suspension (w/v) as follows: (a) twice with 5 ml of 0.1 M Tris-chloride, pH 8.0, containing 5% (w/v) bovine serum albumin and 0.5% (v/v) Triton X-100 TM; (b) once with 5 ml of 0.1 M Tris-chloride, pH 8.0, containing 0.5% (v/v) Triton X-100 and 250 ml of rabbit anti-mouse IgG (Miles Laboratories; ca 2.5 mg of IgG per milliliter); and (c) once with 5 ml of 0.1 M Tris-chloride, pH 8.0, containing 0.5% (v/v) Triton X-100 TM. Finally, the rabbit anti-mouse IgG-*Staphylococcus aureus* is resuspended in 5 ml of the last buffer.

To assay for the presence of PGI$_2$ synthase antibody, either 50 microliters of serum from mice immunized with PGI$_2$ synthase preparations or 200 microliters of medium from a well containing a growing hybridoma (after the medium turns yellow) is mixed wth 0.1 ml of the rabbit anti-mouse IgG-*Staphylococcus aureus* suspension. The mixture is vortexed and centrifuged at 1500 g on a desk-top centrifuge, and the supernatant is removed by aspiration. After resuspending the cell pellet in 0.5 ml of 0.1 M Tris-chloride, pH 8.0 containing 0.5% Triton X-100 TM, solubilized PGI$_2$ synthase (ca 15 units) is added. The PGI$_2$ synthase used in this screening assay is obtained from solubilized microsomes prepared as described above, but prior to chromatography on DE-52. The mixture is vortexed briefly and again the *Staphylococcus aureus* cells are pelleted by centrifugation at 1500 g for 5 minutes. The supernatant is removed by aspiration, and the pellet is resuspended a second time in 1 ml of 0.1 M Tris-chloride containing 0.5% Triton X-100. PGI$_2$ synthase activity is then assayed as described below.

Assay of PGI$_2$ Synthase

For PGI$_2$ synthase assay, [$^3$H]PGH$_2$ is synthesized using [5,6,8,9,11,12,14,15-$^3$H-(N)] arachidonic acid (New England Nuclear, Boston, Mass. 62.2 Ci/mmol) diluted to a specific activity of 3.7 microCi/mg (ca 1000 cpm/nmol) with unlabeled arachidonic acid (NuChek Preps, Elysian, Minn.). To assay, 30 nmol of [$^3$H]PGH$_2$ in 10 $\mu$l of dry ice-acetone is evaporated under a stream of N$_2$ in a test tube and enzyme (or resuspendedcomplex) in a total of 1 ml of 0.1 M Tris-chloride, pH 8.0, containing 0.5% Triton X-100 is added to initiate the raaction. After incubating for 1 minute at 24°, the reaction is stopped by adding 7 ml of chloroform-methanol (1:1, v/v); then 1.8 ml of 0.02 M HCl and 3 ml of chloroform are added, and the mixture is mixed vigorously. The aqueous layer is removed by aspiration and the organic layer is evaporated with N$_2$. Finally, the residue is redissolved in 100 microliters of chloroform and applied quantitatively to a 250 $\mu$m silica gel G thinlayer chromatography plate (Analtech) along with authentic 6-keto-PGF$_{1a}$ and PGF$_{2a}$ standards. The plate is developed twice to a height of 20 cm using the upper layer of ethyl acetate-isooctane-acetic acid-H$_2$O (110:50:20:100, v/v/v/v). After drying the plate in air, the standards are visualized with I$_2$ vapor. The region corresponding to 6-keto-PGF$_{1\alpha}$ is marked, and the rest of each vertical lane is divided into three or four regions. All areas are then scraped into individual scintillation vials, and samples are counted in 7 ml of Bray's solution. The percentage of counts chromatographing with authentic 6-keto-PGF$_{1a}$ is determined, and the nanomoles of PGI$_2$ formed are calculated (nanomoles of [$^3$H]PGH$_2$ in the reaction mixture times the percentage of radioactivity chromatographing with 6-keto-PGF$_{1\alpha}$). Under maximal conditions as much as 85% of PGH$_2$ can be converted to PGI$_2$.

It must be noted that this assay does not yield a well-defined rate. One reason is that the substrate concentration is not saturating at all times, since in a typical assay 40-60% of substrate is converted to product. Also the reaction rate is not linear over the entire assay time, possibly because PGI$_2$ synthase is inactivated during the reaction. However, the assay does provide a convenient estimation of relative enzyme activities and is useful for purification and for screening sera and hybridoma media for antibodies to PGI$_2$ synthase.

Hybridomas Producing Monoclonal Antibodies to PGI$_2$ Synthase

The medium from two of 75 hybridoma-containing wells from a single fusion was found to precipitate PGI$_2$ synthase activity, and cells from these wells were cloned to form two anti-PGI$_2$ synthase antibody-producing cell lines, isn-1 and isn-3. (ATCC HB 8123 and HB8122 respectively). Both hybridomas secrete a mouse IgG$_1$ as determined by Ouchterlony double diffusion using subclass specific antisera. Each monoclonal antibody will cause the immunoprecipitation of an iodinated protein of molecular weight equal to 50,000 from iodinated, solubilized bovine aortic microsomes.

The two hybridoma lines were grown in media free of bovine IgG, and pure mouse IgG$_1$ was isolated from each medium by chromatography on protein A-Sepharose (Pharmacia). IgG$_1$ (isn-3) was iodinated using Bolton-Hunter reagent. The procedures for isolation and iodination of mouse IgG are described in Example 1.

IgG$_1$ (isn-3) is precipitated after incubation with non-solubilized bovine aortic microsomes and centrifugation at 200,000 g for 30 minutes. Unlabeled IgG$_1$ (isn-3) competes with [$^{125}$I]IgG$_1$ (isn-3) for binding to the microsomes. In contrast, IgG$_1$(isn-1) has no effect on the binding of [$^{125}$I]IgG$_1$ (isn-3) indicating that the IgG$_1$ molecules secreted by isn-3 and isn-1 bind different antigenic sites. Since the two antibodies bind different sites, they can be used in a double-antibody immunoradiometric assay similar to the one developed for the PGH synthase in Example 1.

A complex of IgG$_1$ (isn-1) bound to *Staphylococcus aureus* was prepared by adding 100 microg of purified IgG$_1$ (isn-1) in 0.1 M sodium citrate, pH 7.0, to 1 ml of a 10% suspension of rabbit anti-mouse IgG-*Staphylococcus aureus* cell complex. After 5 minutes the *Staphylo-* coccus aureus cells are pelleted by centrifugation and resuspended in 1 ml of 0.1 M Tris-chloride pH 8.0, containing 0.5% Triton X-100 ™. This IgG$_1$ (isn-1)-*Staphylococcus aureus* complex is stable for at least 2 weeks when stored at 4°.

A standard curve for quantitating PGI$_2$ synthase protein is generated as follows. Aliquots of solubilized bovine aortic microsomes (containing 0–0.05 unit of PGI$_2$ synthase; microsomes solubilized in 0.1 M Tris-chloride, pH 8.0, containing 0.5% Triton X-100) are added to 6×50 mm glass test tubes each containing 100,000 cpm of [$^{125}$I]IgG$_1$ (isn-3) and allowed to stand for 30 minutes at 24°; next, 10 µl of the IgG$_1$ (isn-1)-*Staphylococcus aureus* complex are added and the tubes are vortexed and centrifuged immediately at 1500 g for 10 minutes at 24°. Any long delay (>5 min) before centrifugation will increase the degree of nonspecific precipitation of $^{125}$I to unacceptable levels. After centrifugation, the supernatant is removed by aspiration and the pellets are washed once in 0.5 ml of the solubilization buffer. The washed cell pellets present in the 6×50 mm test tubes are placed in vials and counted on a Beckman Biogamma ™ counter.

Figure 2:
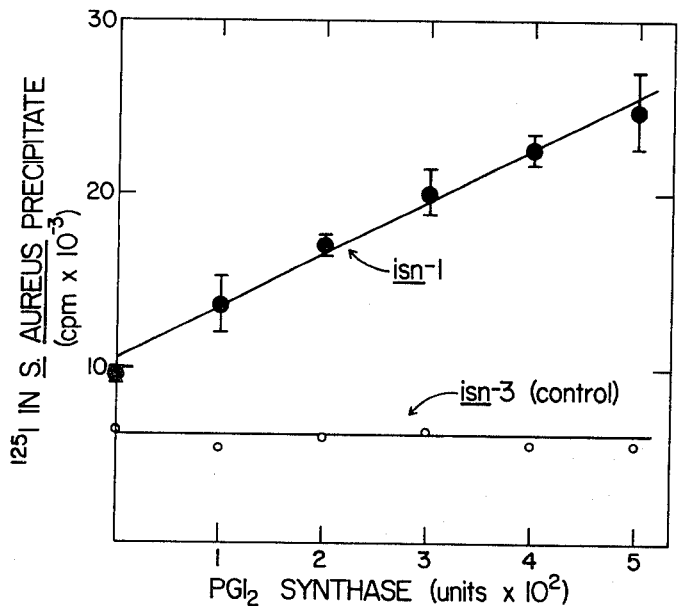
FIG. 2 is a graph showing PGI$_2$ synthase concentration as a function of the first antibody-second antibody complex precipitate.
Figure 4:
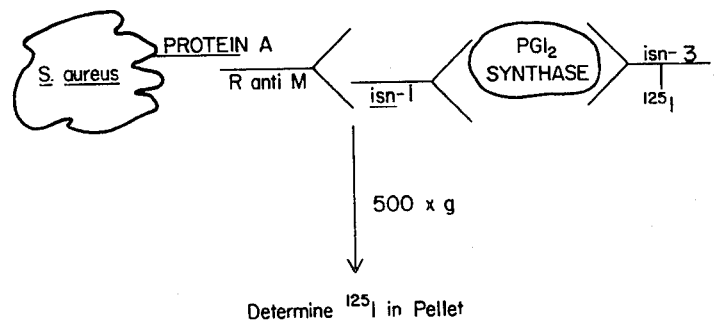
FIG. 4 is an illustration showing the complex of FIG. 2.

A positive linear relationship between precipitated $^{125}$I and added PGI$_2$ synthase activity exists over the range of 0.005–0.05 unit of activity as shown in FIG. 2. FIG. 2 shows an immunoradiometric assay of PGI$_2$ synthase using solubilized bovine aortic microsomes. PGI$_2$ synthase was incubated with [$^{125}$I]IgG$_1$(isn-3) for 30 minutes, then *Staphylococcus aureus* cells conjugated to IgG$_1$ secreted by either isn-1 (●—●) or isn-3 (○—○) was added. The *Staphylococcus aureus* were pelleted by centrifugation and washed, and precipitated $^{125}$I was quantitated. Results are averages of triplicates (●—●); error bars ±SD. FIG. 4 shows the complex formed.

The slope is equal to 300,000 cpm precipitated per unit of PGI$_2$ synthase. This assay is approximately 50–100 times more sensitive than the enzyme activity assays. When IgG$_1$ (isn-3)-*Staphylococcus aureus* complexes are used as controls for IgG$_1$ (isn-1)-*Staphylococcus aureus* cells, no $^{125}$I above background is precipitated.

This immunoradiometric assay provides a simple, sensitive, and highly specific method for quantitating PGI$_2$ synthase. The method is useful for measuring changes in PGI$_2$ synthase protein concentrations in tissues during physiological stresses such as aging and the development of atherosclerosis. The antibodies should also be of value in the immunocytochemical localization of PGI$_2$ synthase at both the cellular and subcellular levels.

It will be appreciated that the second antibody can be the first antibody modified to not bind protein A by removal of the Fc portion of the molecule to leave the Fab portion. Enzymatic digestion of the antibodies with papain in 2-mercaptoethanol produces the fragments. All of this is known to those skilled in the art.

We claim:

1. In a method for determination of polyvalent antigens by reaction with monoclonal antibodies specific for the antigen, wherein the antigen has at least two separate different combining sites for the antibodies the improvement which comprises:

(a) providing a first murine IgG monoclonal antibody which combines with a first antigen combining site and which is bound to an immobilizing carrier by means of *Staphylococcus aureus* Protein A directly or indirectly by means of a conjugal antibody between the IgG antibody and the protein A and a solution containing a second murine IgG monoclonal antibody which combines with a second combining site on the antigen and not to the carrier and which is labeled so as to be detectable, wherein the antibodies are produced by different hybridoma cells and are specific for the same polyvalent antigen but having different combining sites on the antigen, and wherein the second antibody does not react with Protein A or reacts only slowly with Protein A so as not to interfere with determination of the antigen;

(b) reacting the antigen in a solution with the first antibody bound to the carrier to provide a first antibody-antigen complex with the carrier;

(c) reacting the first complex with the second antibody in a solution to provide a first and second antibody-antigen complex with the carrier which is separable from the solution;

(d) separating the first antibody-second antibody-antigen complex from unbound second antibody in solution; and (e) determining the presence of label in the first antibody-second antibody-antigen complex.

2. The method of claim 1 wherein the carrier contains Protein A of killed *Staphylococcus aureus* cells, wherein the first antibody binds to the Protein A and the antigen and wherein the second antibody does not bind to Protein A in the presence of the antigen.

3. The method of claim 2 wherein the carrier is attenuated cells of *Staphylococcus aureus* ATCC 12598.

4. The method of claim 2 wherein the carrier is Protein A sepharose.

5. The method of claim 1 wherein the antigen is PGH synthase.

6. The method of claim 1 wherein the antigen is PGI$_2$ synthase.

7. The method of claim 1 wherein the carrier is attenuated cells of *Staphylococcus aureus* containing protein A, wherein the antigen is PGH synthase and wherein the second antibody does not bind the protein A in the presence of the antigen and the first antibody does bind protein A.

8. The method of claim 1 wherein the carrier is attenuated cells of *Staphylococcus aureus* carrier protein A complexed with a conjugal anti-mouse antibody which binds the protein A and which binds the first antibody which binds the antigen.

9. The method of claim 8 wherein the conjugal antibody is rabbit anti-mouse antibody, wherein the first antibody is secreted by hybridoma cell isn-1 deposited as ATCC No. HB8123 and the second antibody is secreted by hybridoma cell isn-3 deposited as ATCC No. HB 8122.

10. The method of claim 1 wherein the first antibody is secreted by one hybridoma cell selected from cyo 1, 5 and 7 deposited as ATCC HB 8124, HB 8126 and HB 8127, respectively and the second antibody is secreted by hybridoma cell cyo 3 deposited as ATCC HB 8125.

11. The method of claim 1 wherein the first antibody is derived from hybridoma cells isn-1 deposited as ATCC HB 8123 and the second antibody is secreted by hybridoma cell isn-3 deposited as ATCC-HB 8122.

12. As a mercantile kit test kit for a polyvalent antigen which comprises in combination:

(a) a first container containing an IgG monoclonal antibody bound to Protein A immobilized on a second container containing a carrier; and (b) a second container containing a labeled second IgG monoclonal antibody in a solution, wherein in use the amount of the second antibody which combines with the antigen is determined by the label in direct correlation with the amount of antigen, wherein the first and second antibodies are produced by different hybridoma cells and are both specific for the antigen but combine different antigenic determinants on the antigen and wherein the second antibody does not react with Protein A or reacts only slowly with Protein A so as not to interfere with a determination of the antigen.

13. The test kit of claim 12 wherein the carrier is attenuated cells of *Staphylococcus aureus* containing Protein A.

14. The test kit of claim 12 wherein the first antibody is secreted by a hybridoma cell selected from cyo 1, 5 and 7, deposited as ATCC HB 8124, HB 8126, and HB 8127, respectively, wherein the carrier is attenuated cells of *Staphylococcus aureus* containing Protein A and wherein the second labeled antibody is secreted by hybridoma cell cyo-3 deposited as ATCC HB 8125, and does not bind to the protein A of the *Staphylococcus aureus* when complexed with the first antibody.

15. The test kit of claim 12 wherein the carrier is attenuated cells of *Staphylococcus aureus*, wherein the second labeled antibody is secreted by hybridoma cell isn-3 deposited as ATCC HB 8122 with the label added, wherein the first antibody is unlabeled and is secreted by hybridoma cell isn-1 deposited as ATCC HB 8123 and wherein the assay is rapidly completed.

16. The test kit of claim 14 or 15 wherein the label is radioisotope $^{125}$I.

17. Monoclonal antibodies produced by hybridoma cells cyo-1,-3,-5 and -7 and deposited as ATCC HB 8124, HB8125, HB8126 and HB 8127 respectively.

18. Monoclonal antibodies produced by hybridoma cells isn-1 and isn-3 and deposited as ATCC HB8123 and HB8122 respectively.

* * * * *

UNITED STATES PATENT AND TRADEMARK OFFICE
CERTIFICATE OF CORRECTION

PATENT NO. : 4,471,058
DATED : 1984 September 11
INVENTOR(S) : William L. Smith and David L. DeWitt It is certified that error appears in the above-identified patent and that said Letters Patent are hereby corrected as shown below:

Column 8, line 38, "$IgG_{2b}b$" should be --$IgG_{2b}$--.

Column 9, line 67 through Column 10, lines 1 through 8 should be deleted

Column 16, line 47, "carrier" should be --containing--.

Signed and Sealed this

Fourteenth Day of May 1985

[SEAL]

Attest:

DONALD J. QUIGG

Attesting Officer     Acting Commissioner of Patents and Trademarks